United States Patent
Yang et al.

(10) Patent No.: US 10,822,629 B2
(45) Date of Patent: Nov. 3, 2020

(54) POLYPHOSPHATE-DEPENDENT GLUCOKINASE AND METHOD FOR PREPARING GLUCOSE 6-PHOSPHATE BY USING SAME

(71) Applicant: CJ CHEILJEDANG CORPORATION, Seoul (KR)

(72) Inventors: Sung Jae Yang, Suwon (KR); Hyun Kug Cho, Seoul (KR); Young Mi Lee, Suwon (KR); Seong Bo Kim, Seongnam (KR); Seung Won Park, Yongin (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/080,641

(22) PCT Filed: Feb. 6, 2017

(86) PCT No.: PCT/KR2017/001267
§ 371 (c)(1),
(2) Date: Aug. 28, 2018

(87) PCT Pub. No.: WO2017/150814
PCT Pub. Date: Sep. 8, 2017

(65) Prior Publication Data
US 2019/0078125 A1    Mar. 14, 2019

(30) Foreign Application Priority Data
Feb. 29, 2016    (KR) .................. 10-2016-0024293

(51) Int. Cl.
*C12P 19/02*    (2006.01)
*C12N 15/52*    (2006.01)
*C12N 15/70*    (2006.01)
*C12N 9/16*    (2006.01)

(52) U.S. Cl.
CPC .............. *C12P 19/02* (2013.01); *C12N 9/16* (2013.01); *C12N 15/52* (2013.01); *C12N 15/70* (2013.01); *C12Y 207/01002* (2013.01)

(58) Field of Classification Search
CPC ........... C12P 19/02; C12N 9/16; C12N 15/70; C12N 15/52; C12Y 207/01002
See application file for complete search history.

(56) References Cited

U.S. PATENT DOCUMENTS 10,138,506 B2 *  11/2018  Wichelecki .... C12Y 207/01144
2016/0002672 A1     1/2016  Beck et al.

FOREIGN PATENT DOCUMENTS

| CN | 104673855 A | 6/2015 |
| JP | S5272881 A | 6/1977 |
| JP | 2014-064513 A † | 4/2014 |
| KR | 10-1361688 B1 | 2/2014 |

OTHER PUBLICATIONS

Banerjee et al., Improving enzymes for bioness conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directedevolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Liao et al., One-step purification and immobilization of thermophilic polyphosphate glucokinase from Thermobifida fusca YX: glucose-6-phosphate generation without ATP. Appl Microbiol Biotechnol., 2012, vol. 93: 1109-1117. (Year: 2012).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Campbell, Alisha G. et al., "Diversity and genomic insights into the uncultured Chloroflexi from the human microbiota", Environmental Microbiology, 2014, pp. 2635-2643, vol. 16, No. 9, Society for Applied Microbiology and John Wiley & Sons Ltd.
GenBank Accession Number: AP012029, "Anaerolinea thermophola UNI-1 DNA, complete genome", Jun. 3, 2011, pp. 1-2.
Hehuan Liao et al., "One-step purification and immobiliazation of thermophilic polyphosphate glucokinase from Thermobifida fusca YX: glucose-6-phosphate generation without ATP", Applied Microbiology Biotechnology, Jul. 16, 2011, pp. 1109-1117, vol. 93, No. 3, Springer-Verlag.

(Continued)

*Primary Examiner* — Ganapathirama Raghu

(57) ABSTRACT

The present invention relates to a novel high-temperature active thermoresistant polyphosphate-dependent glucokinase with high thermal stability, a composition including the enzyme, and methods for producing glucose 6-phosphate using the enzyme.

10 Claims, 6 Drawing Sheets
Specification includes a Sequence Listing.

(56) References Cited

OTHER PUBLICATIONS

International Search Report for International Patent Application No. PCT/KR2017/001267, dated May 11, 2017.
Mewis, Keith et al., "Biomining active cellulase from a mining bioremediation system", Journal of Biotechnology, 2013, pp. 462-471, vol. 167, Elsevier.
Database UniProtKB [Online], "Polyphosphate-glucose phosphotransferase", UniProtKB: E8MXP4, Apr. 5, 2011, pp. 1-3.
Sekiguchi, Yuji et al., "*Anaerolinea thermophila* gen. nov., sp. nov. and *Caldilinea aerophila* gen. nov., sp. nov., novel filamentous theromophiles that represent a previously uncultured lineage of domain Bacteria at the subphylum vevel", International Journal of Systematic and Evolutionary, Microbiology, 2003, pp. 1843-1851, vol. 53.
NCBI, GenBank, Accession No. AP012029.1, Jan. 25, 2011, pp. 1-332.
Santos, Helena et al., "Characterization and Quantification of Compatible Solutes in (Hyper) thermophilic Microorganisms", Methods in Microbiology., 2006. 35:173-199.
Esteves, Ana et al. "Mannosylglycerate and Di-myo-Inositol Phosphate have Interchangeable Roles during Adaptation of Pyrococcus furiosus to Heat Stress" Appl. Environ. Microbiol. doi:10.1128/AEM.00559-14, May 2014, 28 pages.
Wang, Quanhui et al. "The Survival Mechanisms of Thermophiles at High Temperatures: An Angle of Omics", Physiology 30, Mar. 2015, 97-106.
Lamosa, Pedro et al., "Thermostabilization of Proteins by Diglycerol Phosphate, a New Compatible Solute from the Hyperthermophile Archaeoglobus fulgidus", Appl. Environ. Microbiol. May 2000, pp. 1974-1979.
Roger R. Gomis et al., "Glucose 6-Phosphate Produced by Gluconeogenesis and by Glucokinase Is Equally Effective in Activating Hepatic Glycogen Synthase", Journal of Biological Chemistry, vol. 278, No. 11, Jan. 7, 2003, pp. 9740-9746, XP55625888.
S. Narita-Yamada et al., "Whole genome sequence of Anaerolinea thermophila UNI-1", Apr. 5, 2011, XP055625730, URL:https://www.uniprot.org/uniprot/E8MXP4.txt.
Tanaka Shotaro et al., "Strictly Polyphosphate-Dependent Glucokinase in a Polyphosphate-Accumulating Bacterium, Microlunatus Phosphovorus", Journal of Bacteriology, vol. 185, No. 18, Sep. 1, 2003, pp. 5654-5656, XP002455620.
Taniguchi Hajime, "Enzymatic Degradation of Starch", Applied Carbohydrate Science, 2011, vol. 1, No. 1, pp. 17-22.
Albi, Tomas et al., "Two strictly polyphosphate-dependent gluco(manno)kinases from diazotropic Cyanobacteria with potential to phosphorylate hexoses from polyphosphates", pp. 3887-3900, Nov. 9, 2014, Applied Microbiology and Biotechnology vol. 99, Issue 9.†

\* cited by examiner
† cited by third party

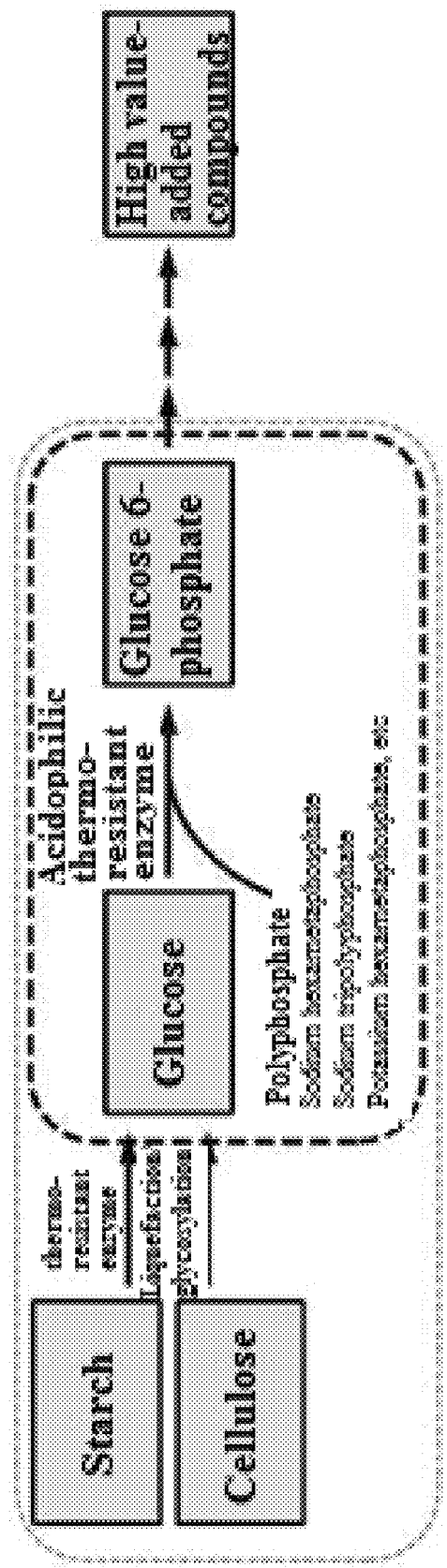
[ FIG. 1 ]

[ FIG. 2 ]
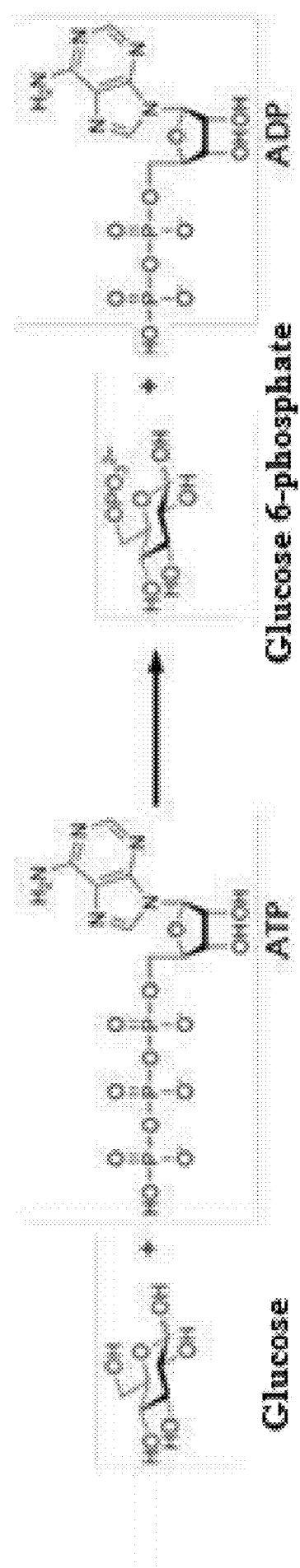

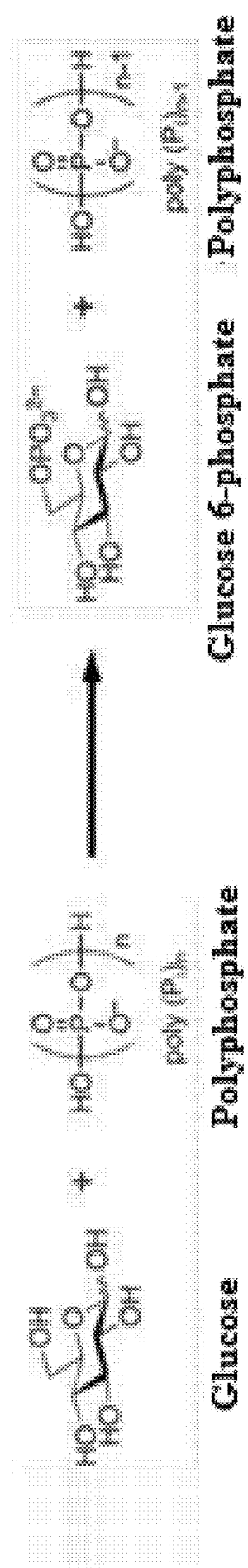
[ FIG. 3 ]

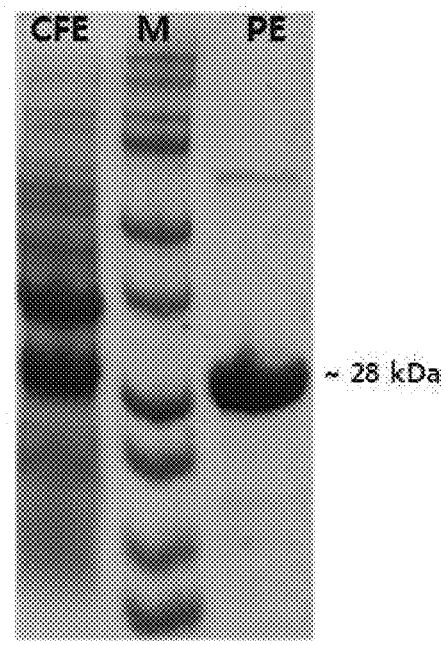
[FIG. 4]

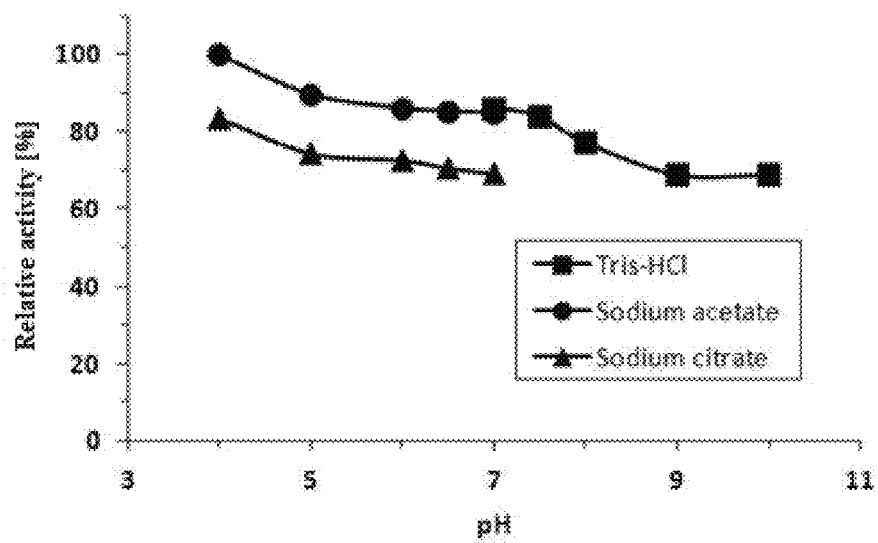
[FIG. 5]
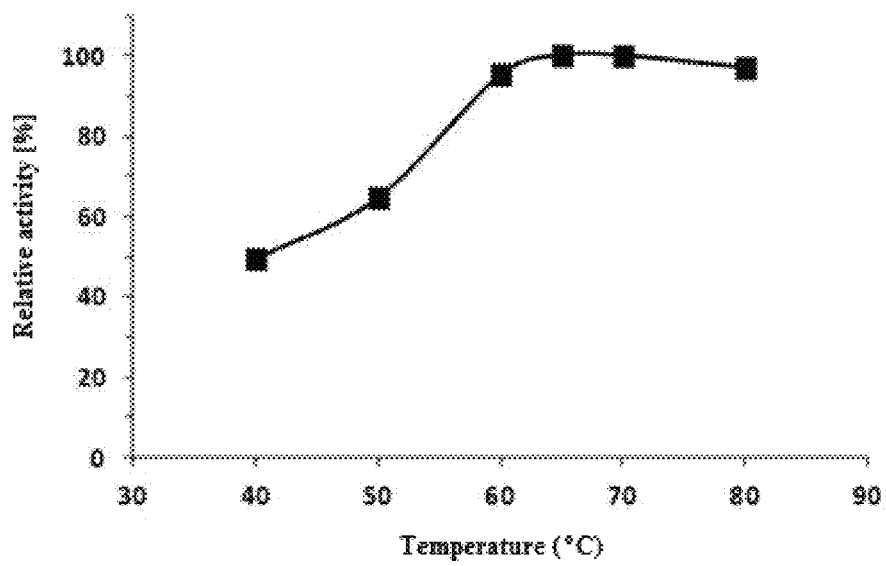
[FIG. 6]

[FIG. 7]
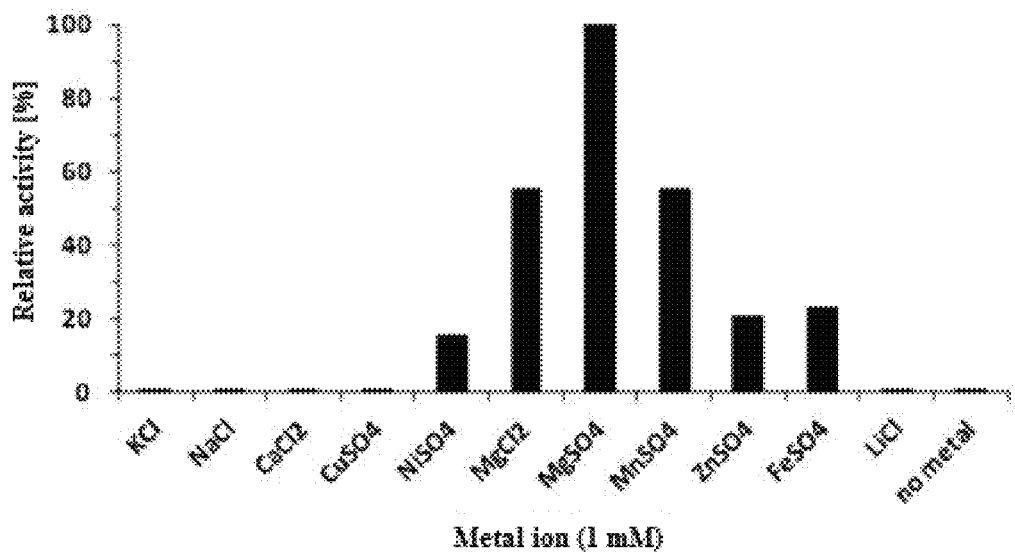
[FIG. 8]
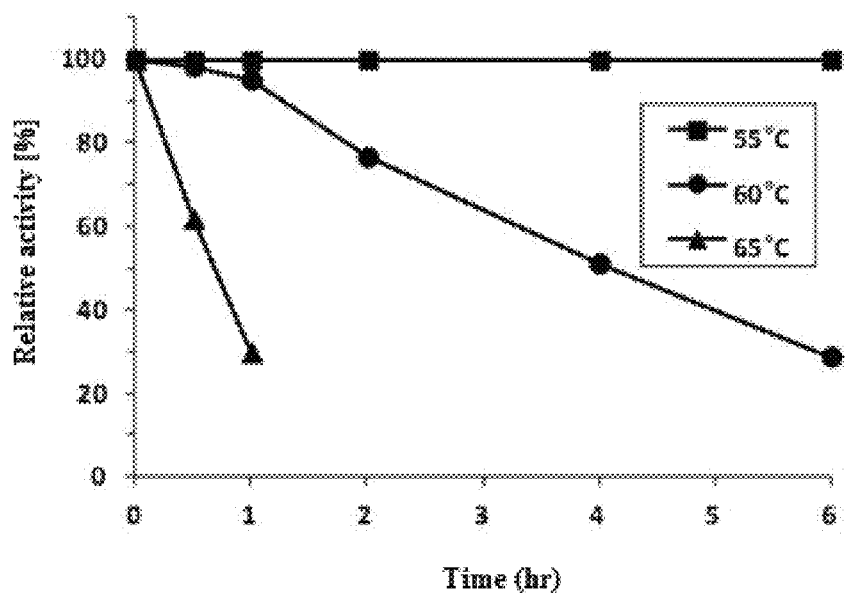

SEQUENCE LISTING

<160> NUMBER OF SEQ ID NOS: 4

<210> SEQ ID NO 1
<211> LENGTH: 762
<212> TYPE: DNA
<213> ORGANISM: Anaerolinea thermophila

<400> SEQUENCE: 1

```
atggggaggc agggcatgga aattttaggg attgatatcg gaggatccgg catcaaaggg      60
gctccggtgg atgtagaaac cggccagtta accgccgagc gataccgctt acccaccccc     120
gaaaatgcct tacctgaaga agtggctctg gtagttgccc aaattgtcga acactttcag     180
tggaaaggtc gtgtaggggc aggatttcct gctgccatca gcacggcgt ggcacagacg      240
gccgcaaaca tccaccctac atggattgga cttcatgctg caaccttt cagcgaaaaa       300
tgcggatgtc ctgtctcagt gttgaatgat gcggatgctg ccggactggc ggaaatgatc     360
tttgggcag gaaaaggcca gaaggggtg gtgctgatga ttaccattgg cactggcatc       420
gggacagccc tgttcaccga tgggatattg gtccctaata ccgagttggg acatattgaa     480
attcgggca aagatgccga acagcgctct tcggaagccg cccgccagcg gaaggattgg      540
acctggcaac aatgggcaaa gcgtctgaat gagcatttgg agcgcctgga gccctgttc      600
tggcccgatt tattcatcct tggtggaggg gcagtaaaaa atcatgaaaa gttcttccct     660
tatctaaaac tgcgtactcc ctttgttgca gcaaaattgg ggaatctggc tgggattgta     720
ggcgcagcgt ggtatgctca cacccaggaa acgcaagcct ga                        762
```

<210> SEQ ID NO 2
<211> LENGTH: 253
<212> TYPE: PRT
<213> ORGANISM: Anaerolinea thermophila

<400> SEQUENCE: 2

```
Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Gly Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190
```

```
Leu Glu Arg Leu Glu Ala Leu Phe Trp Pro Asp Leu Phe Ile Leu Gly
        195                 200                 205

Gly Gly Ala Val Lys Asn His Glu Lys Phe Phe Pro Tyr Leu Lys Leu
        210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
                245                 250

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
caccatatgg ggaggcaggg catggaaatt ttag                          34

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
caaactcgag ggcttgcgtt tcctgggtg                                29
```

POLYPHOSPHATE-DEPENDENT GLUCOKINASE AND METHOD FOR PREPARING GLUCOSE 6-PHOSPHATE BY USING SAME

CROSS-REFERENCE TO RELATED APPLICATIONS

The present specification is a U.S. National Stage of International Patent Application No. PCT/KR2017/001267 filed Feb. 6, 2017, which claims priority to and the benefit of Korean Patent Application No. 10-2016-0024293 filed in the Korean Intellectual Property Office on Feb. 29, 2016, the entire contents of which are incorporated herein by reference.

TECHNICAL FIELD

The present invention relates to a novel polyphosphate-dependent glucokinase, a composition comprising the glucokinase, and methods for producing glucose 6-phosphate using the glucokinase.

BACKGROUND ART

D-glucose 6-phosphate is a major phosphorylation product of the biological metabolism and is industrially very useful because it can be converted into various valuable metabolites through the glycolysis pathway, the pentose phosphate pathway, and the hexosamine biosynthetic pathway. The development of economic methods for producing glucose 6-phosphate is of great importance in biological processes for producing specific high value-added compounds from glucose 6-phosphate through a series of multiple enzymatic reactions.

According to previously published reports, D-glucose 6-phosphate is enzymatically produced using an ADP-dependent glucokinase (EC 2.7.1.147) transferring the β-phosphate group of adenosine diphosphate (ADP) to D-glucose as a raw material, an ATP-dependent glucokinase (EC 2.7.1.2) transferring the γ-phosphate group of adenosine triphosphate (ATP) to D-glucose as a raw material, or a polyphosphate (poly(Pi)$_n$)-dependent glucokinase (EC 2.7.1.63) transferring phosphate groups of polyphosphate (poly(Pi)$_n$) to D-glucose as a raw material.

The method for producing glucose 6-phosphate using an ADP/ATP-dependent glucokinase requires expensive ADP or ATP as a phosphate donor (see Reaction Scheme 1) and is thus disadvantageous in terms of economic efficiency and stability. In an attempt to overcome this disadvantage, an ADP/ATP-dependent glucokinase is used in combination with a polyphosphate-AMP/ADP phosphotransferase capable of transferring phosphate groups from Poly(Pi)$_n$ to AMP or ADP as a dephosphorylation product to recover ADP or ATP. However, this attempt is also limited in practical use due to low physical and chemical (heat, pH, etc.) stabilities of the adenine nucleotides AMP, ADP, and ATP.

[Reaction Scheme 1]

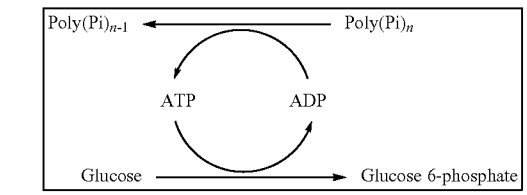

According to the method using a polyphosphate-dependent glucokinase, Poly(Pi)$_n$ is used as a phosphate donor to directly produce glucose 6-phosphate (see Reaction Scheme 2). The use of relatively inexpensive and stable Poly(Pi)$_n$ makes this method advantageous from the viewpoint of economic and commercial efficiency over the method using an ADP/ATP-dependent glucokinase.

[Reaction Scheme 2]

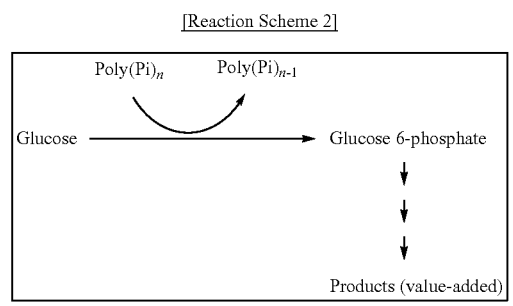

DISCLOSURE

The Sequence Listing created on Aug. 28, 2018 with a file size of 4 KB, and filed herewith in ASCII text file format as the file entitled "40Q2037.TXT," is hereby incorporated by reference in its entirety.

Technical Problem

The present invention is directed to a polyphosphate-dependent glucokinase, a composition comprising the glucokinase, and methods for producing glucose 6-phosphate using the glucokinase. The stability of an enzyme is a very important requirement in terms of efficiency for the enzymatic production of a specific compound. To date, however, a limited number of polyphosphate-dependent glucokinases related to the present invention have been reported in some microbial species. Most of the isolated enzymes were derived from mesophilic microorganisms and thus showed low thermal stability (Table 1). The present invention has been made in an effort to solve the above problems, and it is one object of the present invention to provide a novel thermophilic and thermoresistant polyphosphate-dependent glucokinase derived from a thermophile, a composition comprising the enzyme, and methods for producing glucose 6-phosphate using the enzyme.

TABLE 1

| Microorganism | Optimum temp. & thermal stability | Reference |
|---|---|---|
| *Mycobacterium phlei* | 3° C., 24 h, 50% of its activity was lost | 1957. Bull Acad Pol Sci Ser Sci Biol. 5: 379-381<br>1964. Biochem Biophys Acta. 85: 283-295 |

TABLE 1-continued

| Microorganism | Optimum temp. & thermal stability | Reference |
|---|---|---|
| Corynebacterium diphtheria | Not reported | 1961. Bull Acad Pol Sci Ser Sci Bioi. 9: 371-372 |
| Mycobacteria | Not reported | 1978. Acta Microbiol Pol. 27: 73-74 |
| Nocardia minima | Not reported | 1979. Acta Microbiolog Pol. 28: 153-160 |
| Propionibacterium shermanii | Not reported | 1986. J Bio Chem. 261: 4476-4480 |
| Mycococcus coralloudes | Not reported | 1990. Arch Microbiology 154: 438-442 |
| Mycobacterium tuberculosis | Not reported | 1996. Biochemistry. 35: 9772-81. |
| Microlunatus phosphovorus | Optimally active at 30° C. 25° C., 5 min, 50% of its activity was lost | 2003. J Bacteriol. 185: 5654-5656 2011. Appl Microbiol Biotechnol. 93: 1109-1117 |
| Arthrobacter sp. KM | Optimally active at 45° C. 40° C., 5 min, 50% of its activity was lost | 2003. Appl Environ Microbiol. 69: 3849-3857 2004. J Bioi Chem 279: 50591-50600 |
| Corynebacterium glutamicum | 50° C., 60 min, 88% of activity lost | 2010. Appl Microbiol Biotechnol. 87: 703-713 |
| Thermobifida fusca | 50° C. 25 min, 50% of its activity was lost Optimally active at 55° C. | 2011 Appl Microbiol Biotechnol. 93: 1109-1117 |
| Streptomyces coelicolor A3(2) | Optimally active at 28° C. | 2013 Biosci Biotechnol Biochem 77: 2322-2324 |
| Anabaena sp. PCC 7120 | Optimally active at 28° C. | 2014. Microbiology. 160: 2807-2819 |

Glucose 6-phosphate is a major phosphorylation product of the glycolysis pathway and the pentose phosphate pathway in the biological metabolism. Glucose 6-phosphate is industrially very useful because it can be converted into various metabolites. More effective methods for producing glucose 6-phosphate are necessary to produce high value-added compounds from glucose 6-phosphate through a series of multiple enzymatic reactions.

ATP or ADP is usually used as a phosphate donor for enzymatic conversion of glucose to glucose 6-phosphate in the biological metabolism. However, its high cost is an obstacle to the development of effective processes for the production of glucose 6-phosphate via the enzymatic reaction pathway. Further, microbial fermentation is not suitable for the production of glucose 6-phosphate because the produced glucose 6-phosphate can not readily cross cell membranes and can be dephosphorylated by various cellular phosphatases.

Polyphosphate (Poly(Pi)$_n$) as a phosphate donor is plentiful in nature or can be economically produced by chemical processes and thus has been considered a commercially valuable compound. Therefore, the development of an efficient method for enzymatic production of glucose 6-phosphate from glucose using Poly(Pi)$_n$ is commercially very important.

However, most of the previously reported enzymes for glucose 6-phosphate production using Poly(Pi)$_n$ react at a relatively low temperature and have low thermal stability, limiting their application to the production of glucose 6-phosphate.

Technical Solution

The present invention is aimed at providing a novel thermophilic and thermoresistant polyphosphate-dependent glucokinase derived from a thermophile and methods for producing glucose 6-phosphate using the enzyme.

Numerous aspects of the present invention will now be described in detail.

One aspect of the present invention provides a thermophilic and thermoresistant polyphosphate-dependent glucokinase derived from the genus Anaerolinea.

Specifically, the polyphosphate-dependent glucokinase of the present invention may have the amino acid sequence set forth in SEQ ID NO. 2. The polyphosphate-dependent glucokinase of the present invention may be any protein that has an amino acid sequence having a homology of at least 70%, specifically at least 80%, more specifically at least 90%, even more specifically at least 95% to the amino acid sequence set forth in SEQ ID NO. 2 and is protein substantially identical or corresponding to a polyphosphate-dependent glucokinase. In addition, if such homology sequence is an amino acid sequence which substantially exhibits the function of polyphosphate-dependent glucose phosphorylation, even a protein variant whose amino acid sequence is partially deleted, modified, substituted or added is of course within the scope of the present invention.

As used herein, the term "homology" refers to the degree of identity or correspondence between given polypeptide sequences or polynucleotide sequences that may or may not share a common evolutionary origin and may be expressed as a percentage. In the present specification, a homology sequence having an identical or similar activity to a given polypeptide or polynucleotide sequence is expressed as "% homology". For example, the homology may be determined using a standard software, specifically BLAST 2.0, to calculate parameters such as score, identity, and similarity. Or, the homology may be identified by comparing sequences by a Southern hybridization experiment under defined stringent conditions. The defined appropriate hybridization conditions may be determined by methods well known to those skilled in the art (see Sambrook et al., 1989, infra). In one embodiment, two amino acid sequences are judged to be "substantially homologous" or "substantially similar" when at least 21% (specifically at least about 50%, particularly about 75%, 90%, 95%, 96%, 97% or 99%) of the polypeptides match over the defined length of the amino acid sequences.

Another aspect of the present invention provides the polynucleotide encoding a thermoresistant polyphosphate-dependent glucokinase derived from the genus Anaerolinea. Specifically, the present invention may provide the polynucleotide sequence which encodes a protein having the activity of a polyphosphate-dependent glucokinase and represents by SEQ ID NO. 1.

As used herein, the term "polynucleotide" refers to a polymer of nucleotide units that are linked covalently to form a long chain. Generally, the polynucleotide means a DNA or RNA strand whose length is above a predetermined level.

The polynucleotide encoding a protein having the activity of a polyphosphate-dependent glucokinase may include a polynucleotide sequence encoding the amino acids shown in SEQ ID NO. 2. Various modifications may be made in the coding region of the polynucleotide as long as the amino acid sequence of the polypeptide is not altered due to the degeneracy of codons or in consideration of preferential codons in an organism where the enzyme is to be expressed. For example, the polynucleotide may have the sequence set forth in SEQ ID NO. 1. The polynucleotide may have a nucleotide sequence having a homology of at least 70%, specifically at least 80%, more specifically at least 90%, even more specifically at least 95%, most specifically at least 98% to the sequence set forth in SEQ ID NO. 1 and can substantially encode a polypeptide having a polyphosphate-dependent glucose phosphorylation activity. It is apparent that a variant whose amino acid sequence is partially deleted, modified, substituted or added is also within the scope of the present invention.

A composition for producing glucose 6-phosphate including 1% to 3% by weight of glucose, 1% to 10% by weight of polyphosphate, 10 U/ml to 50 U/ml of the polyphosphate-dependent glucokinase, and optionally 1 mM to 20 mM magnesium ions (e.g., $MgSO_4$ or $MgCl_2$) based on the total volume of the composition can achieve a conversion yield of at least 70%, more specifically at least 80%, even more specifically at least 90%, to glucose 6-phosphate.

Specifically, a composition including 2% by weight of glucose, 1.5% by weight of polyphosphate, 10 U/ml to 50 U/ml of the polyphosphate-dependent glucokinase, and optionally 10 mM $MgSO_4$ can achieve a conversion yield of at least 60%, more specifically at least 70%, even more specifically at least 80%, to glucose 6-phosphate.

A composition for producing glucose 6-phosphate including 5% to 20% by weight of glucose, 5% to 12% by weight of polyphosphate, 10 U/ml to 50 U/ml of the polyphosphate-dependent glucokinase, and optionally 1 mM to 20 mM magnesium ions (e.g., $MgSO_4$ or $MgCl_2$) based on the total volume of the composition can achieve a conversion yield of at least 50%, more specifically at least 60%, even more specifically at least 70%, to glucose 6-phosphate.

Specifically, a composition including 15% by weight of glucose, 10% by weight of polyphosphate, 10 U/ml to 50 U/ml of the polyphosphate-dependent glucokinase, and optionally 10 mM $MgSO_4$ based on the total volume of the composition can achieve a conversion yield of at least 50%, more specifically at least 60%, even more specifically at least 65%, to glucose 6-phosphate.

The polyphosphate-dependent glucokinase may be active at a temperature of 45° C. to 90° C., more specifically 55° C. to 80° C., most specifically 65° C. to 70° C.

The polyphosphate-dependent glucokinase may be active at a pH of 4 to 10, most specifically at a pH of 4 to 5.

The activity of the polyphosphate-dependent glucokinase may be enhanced in the presence of magnesium ions.

The magnesium ions may be specifically present at a concentration of 0.5 mM to 20 mM, more specifically 0.2 mM to 10 mM, even more specifically 1 mM.

A further aspect of the present invention provides a composition for the production of glucose 6-phosphate including the polyphosphate-dependent glucokinase described herein, glucose, and polyphosphate.

The composition may further include magnesium ions. The composition may be used for the production of glucose 6-phosphate. The ingredients used in this aspect and their contents are the same as those described in the previous and following aspects, and a detailed description thereof is thus omitted.

Yet another aspect of the present invention provides a method for producing glucose 6-phosphate from a composition including the polyphosphate-dependent glucokinase described herein, glucose, and polyphosphate.

The reaction for the production of glucose 6-phosphate is carried out at a temperature of 45° C. to 90° C. and a pH of 4 to 10.

The glucose may be prepared by liquefaction or saccharification of starch or cellulose.

The polyphosphate serves as a phosphate donor, and examples thereof include sodium hexametaphosphate, sodium tripolyphosphate, and potassium hexametaphosphate, but are not limited thereto, they also include commercially available one.

The glucose 6-phosphate may be produced at a temperature of 45° C. to 90° C., more specifically 55° C. to 80° C., most specifically 65° C. to 70° C.

The polyphosphate-dependent glucokinase may have a molecular weight of 10 kDa to 100 kDa, specifically 20 kDa to 50 kDa.

The composition may further include magnesium ions. For example, a source of the magnesium ions may be $MgCl_2$ or $MgSO_4$. Specifically, the composition may further include $MgSO_4$.

The polyphosphate-dependent glucokinase may be present in an amount of 10 U/ml to 50 U/ml.

The glucose may be present in an amount of 0.1% to 40% by weight, more specifically 1% to 20% by weight, most specifically 1% to 10% by weight, based on the total volume of the composition.

The polyphosphate may be present in an amount of 0.5% to 25% by weight, more specifically 1% to 20% by weight, most specifically 1% to 10% by weight, based on the total volume of the composition.

Yet another aspect of the present invention provides a method for producing glucose 6-phosphate from a composition including the polyphosphate-dependent glucokinase described herein, liquefying and saccharifying enzymes, starch, and polyphosphate.

The reaction for the production of glucose 6-phosphate is carried out at a temperature of 45° C. to 90° C. and a pH of 4 to 10.

The liquefying and saccharifying enzymes may be one or more selected from alpha-amylases, glucoamylases and alpha-glycosidases.

Yet another aspect of the present invention provides a microorganism producing the polyphosphate-dependent glucokinase. Specifically, the microorganism of the present invention belongs to the genus *Escherichia*.

As used herein, the term "microorganism producing the polyphosphate-dependent glucokinase" refers to a prokaryotic or eukaryotic microbial strain that can produce the enzyme therein. Specifically, the microorganism producing the polyphosphate-dependent glucokinase is a microorganism capable of accumulating the enzyme in a medium or therein by genetic engineering or natural mutation.

The microorganism is not specifically limited and may be any one that can express the polypeptide having the sequence set forth in SEQ ID NO. 2. The microorganism may be a prokaryotic or eukaryotic microorganism, specifically a prokaryotic microorganism. Examples of such prokaryotic microorganisms include, but are not limited to, microbial strains belonging to the genera *Escherichia, Erwinia, Serratia, Providencia, Corynebacterium*, and *Brevibacterium*. Specifically, the microorganism may be one belonging to the genus *Escherichia*. A non-limiting example of the microorganism belonging to the genus *Escherichia* is *Escherichia coli*.

As used herein, the term "expression" refers to a process in which a polynucleotide encoding the polypeptide of the present invention is transformed with a operable recombinant vector or is inserted into a chromosome. The expression process is not particularly limited.

As used herein, the term "transformation" refers to the introduction of a vector including a polynucleotide encoding a target protein into a host cell to express the protein encoded by the polynucleotide in the host cell. The transfected polynucleotide may be either inserted into and located in the chromosome of the host cell or may exist extrachromosomally as long as it can be expressed in the host cell. The polynucleotide includes DNA and RNA encoding the target protein. The polynucleotide may be introduced in any form as long as it can be introduced into and expressed in the host cell. For example, the polynucleotide may be introduced into the host cell in the form of an expression cassette, which is a gene construct including all elements required for its autonomous expression, but its form is not limited thereto. Typically, the expression cassette includes a promoter operably linked to the polynucleotide, a transcription termination signal, a ribosome-binding domain, and a translation termination signal. The expression cassette may be in the form of a self-replicable expression vector. The polynucleotide as it is may be introduced into the host cell and operably linked to sequence required for expression in the host cell.

As used herein, the term "operably linked" refers to a functional linkage between a promoter sequence which initiates and mediates the transcription of the polynucleotide encoding the target protein of the present invention and the gene sequence.

As used herein, the term "vector" refers to any vehicle for the cloning of and/or transfer of base sequence into a host cell. A vector may be a replicon to which another DNA segment may be attached so as to bring about the replication of the attached segment. A "replicon" refers to any genetic element (e.g., plasmid, phage, cosmid, chromosome or virus) that functions as an autonomous unit of DNA replication in vivo, i.e. capable of replication under its own control. The term "vector" may include both viral and nonviral vehicles for introducing base sequence into a host cell in vitro, ex vivo or in vivo. The term "vector" may also include minicircle DNAs. For example, the vector may be a plasmid without bacterial DNA sequences. The removal of bacterial DNA sequences which are rich in CpG regions has been shown to decrease silencing of transgene expression and result in more persistent expression from plasmid DNA vectors (e.g., Ehrhardt, A. et al. 2003. HumGene Ther 10: 215-25; Yet, et al. 2002. Mol Ther 5: 731-38; Chen et al. 2004, Gene Ther 11: 856-864). The term "vector" may also include transposons (Annu Rev Genet. 2003. 37:3-29), or artificial chromosomes. Specific examples of vectors suitable for use in the present invention include, but are not limited to, pACYC177, pACYC184, pCL1920, pECCG117, pUC19, pBR322, and pMW118 vectors. Variants of these vectors, for example, in which promoters are mutated, may also be used in the present invention.

Particularly, the vector in the present invention may be a DMA construct including a polynucleotide sequence encoding the desired protein which is operably linked to an appropriate expression regulatory sequence to express the desired protein in a suitable host cell. The regulatory sequence may include a promoter that can initiate transcription, an optional operator sequence for regulating the transcription, a sequence encoding a suitable mRNA ribosome binding site, and a sequence regulating the termination of transcription and translation. After the vector is introduced into the suitable host cell, it may replicate or function independently of the host genome and may be integrated into the genome itself.

The vector used in the present invention is not particularly limited as long as the vector is replicable in the host cell. The vector may be any of those known in the art. Examples of such known vectors include natural or recombinant plasmids, cosmids, viruses, and bacteriophages. The phage vectors or cosmid vectors may be, for example, pWE15, M13, λE15, λE1515, E15, M13, and Charon21A, but are not limited thereto. The plasmid vectors may be those based on pBR, pUC, pBluescriptII, pGEM, pTZ, pCL, and pET, but are not limited thereto.

The present invention also provides a recombinant expression vector including a gene encoding the polyphosphate-dependent glucokinase.

The present invention also provides *Escherichia coli* BL21(DE3)/CJ_at_ppgk transformed with the recombinant expression vector containing the sequence of SEQ ID NO. 1. The strain was deposited with the Korean Culture Center of Microorganisms on Feb. 16, 2016 under the deposit number KCCM11814P.

The present invention also provides economic methods for producing industrially useful following compounds from polyphosphate and glucose or starch based on one-pot enzymatic conversions using the polyphosphate-dependent glucokinase and additional functional enzymes (e.g., α-amylases, glucoamylases, α-glucosidases, isomerases, aldolases, synthases, kinases, and phosphatases).

Examples of such industrially useful compounds include, but are not limited to, D-glucose 1-phosphate, D-fructose 6-phosphate, D-fructose 1,6-bisphosphate, myo-inositol 3-phosphate, myo-inositol, D-glucuronate, D-glucosamine 6-phosphate, D-glucosamine, N-acetyl-D-glucosamine 6-phosphate, N-acetyl-D-glucosamine, N-acetyl-D-mannosamine 6-phosphate, N-acetyl-D-mannosamine, N-acetyl-neuraminic acid (sialic acid), D-mannose 6-phosphate, D-mannose, D-tagatose 6-phosphate, D-tagatose, D-allulose 6-phosphate, D-allulose, D-glyceraldehyde 3-phosphate, and dihydroxyacetone phosphate. The industrially useful compounds may also include various compounds produced from glucose 6-phosphate.

Advantageous Effects

The enzyme of the present invention can participate in enzymatic reactions at relatively high temperatures. The high reaction temperature increases the solubility of D-glucose and $Poly(Pi)_n$ as substrates, enabling the use of the substrates at high concentrations. In addition, the diffusion rates of the materials and the reaction rate can be increased and the reaction time can be reduced, achieving increased unit productivity. Furthermore, the high reaction temperature can minimize contamination caused by foreign microorganisms during processing. Moreover, the thermal tolerance of the enzyme related to the present invention can be used to readily disrupt enzyme-produced recombinant cells using heat-treatment processes. When the recombinant enzyme is isolated and used, proteins derived from recombinant expression microorganisms can be also selectively denatured and removed, enabling efficient purification of the enzyme.

DESCRIPTION OF DRAWINGS

FIG. 1 is a flowchart illustrating a method for producing glucose 6-phosphate according to the present invention.

FIG. 2 shows a reaction scheme for the production of glucose 6-phosphate from glucose and ATP.

FIG. 3 shows a reaction scheme for the production of glucose 6-phosphate from glucose and polyphosphate.

FIG. 4 shows SDS-PAGE gel images of a supernatant (CFE) after cell disruption, a size marker (M), and a purified recombinant polyphosphate-dependent glucokinase (PE), which were taken after electrophoresis.

FIG. 5 shows the pH-dependent activity of a recombinant polyphosphate-dependent glucokinase.

FIG. 6 shows the temperature-dependent activity of a recombinant polyphosphate-dependent glucokinase.

FIG. 7 shows the activities of a recombinant polyphosphate-dependent glucokinase in the presence of different kinds of metal ions.

FIG. 8 shows the activities of a recombinant polyphosphate-dependent glucokinase when heated to different temperatures.

MODE FOR INVENTION

Glucose is a relatively cheap carbon source and can be mass-produced from starch or cellulose. Glucose is commonly used as a basic raw material in chemical or biological conversion processes for the production of various compounds that are useful in the chemical, pharmaceutical, cosmetic, and food industries.

However, phosphorylated glucose as a basic raw material in biological processes, particularly enzymatic conversion processes, is currently limited in use due to high price thereof.

Glucose 6-phosphate is an industrially pivotal metabolite in glucose metabolism and can be used as a basic raw material that can induce very useful reactions based on the use of various metabolic enzymes present in nature (organisms).

Under these circumstances, the present invention is aimed at providing an enzyme and enzymatic methods for economically producing glucose 6-phosphate, which is a raw material for various industrially useful compounds, from glucose and polyphosphate.

Using the glucose 6-phosphate produced and the producing method of the present invention can also provide high value-added functional compounds in the pharmaceutical, cosmetic, and food industries that can be prepared by the enzymatic methods.

EXAMPLES

Example 1: Production of Recombinant Expression Vector Including Polyphosphate-Dependent Glucokinase Gene and Transformed Microorganism To provide a novel high-temperature active thermoresistant polyphosphate-dependent glucokinase, a polyphosphate-dependent glucokinase gene derived from thermophilic *Anaerolinea thermophila* was isolated, a recombinant expression vector was constructed, and a transformed microorganism was produced.

Specifically, gene sequences associated with the enzyme of the present invention were screened from the gene sequences registered in GenBank and only the gene sequence derived from the thermophilic microorganism was selected therefrom. Based on the registered gene sequence (SEQ ID NO. 1) and the amino acid sequence (SEQ ID NO. 2) of *Anaerolinea thermophila*, a forward primer (SEQ ID NO. 3) and a reverse primer (SEQ ID NO. 4) were designed. The corresponding gene was amplified from *Anaerolinea thermophila* genomic DNA by polymerase chain reaction (PCR) using the synthesized primers. The amplified polyphosphate-dependent glucokinase gene was inserted into plasmid vector pET21a (Novagen) for expression in *E. coli* using restriction enzymes NdeI and XhoI to construct a recombinant expression vector, which was named CJ_at_p-pgk. CJ_at_ppgk was transfected into strain *E. coli* BL21 (DE3) by a general transformation technique (see Sambrook et al. 1989) to produce a transformed microorganism, which was named *E. coli* BL21(DE3)/CJ_at_ppgk.

Example 2: Production of Recombinant Polyphosphate-Dependent Glucokinase

In this example, a recombinant polyphosphate-dependent glucokinase was produced. First, a culture tube containing 5 ml of LB liquid medium was inoculated with *E. coli* BL21(DE3)/CJ_at_ppgk. The inoculum was cultured in a shaking incubator at 37° C. until an absorbance of 2.0 at 600 nm was reached. The culture broth was added to LB liquid medium in a culture flask, followed by main culture. When the absorbance of the culture at 600 nm reached 2.0, 1 mM IPTG was added to induce the expression and production of a recombinant enzyme. The culture temperature was maintained at 37° C. with stirring at 200 rpm. The culture broth was centrifuged at 8,000×g and 4° C. for 20 min to collect bacterial cells. The collected bacterial cells were washed twice with 50 mM Tris-HCl buffer (pH 7.0) and suspended in the same buffer. Then, cells were disrupted using an ultrasonic homogenizer. The cell lysate was centrifuged at 13,000×g and 4° C. for 20 min and only supernatant of the cell lysate was taken. The recombinant enzyme was purified from the supernatant by His-tag affinity chromatography. The purified recombinant enzyme was dialyzed against 50 mM Tris-HCl buffer (pH 7.0) and was then characterized.

In FIG. 4, M indicates a size marker, CFE indicates the supernatant after cell disruption, and PE indicates the purified enzyme. The purified recombinant polyphosphate-dependent glucokinase was found to have a molecular weight of about 28 kDa, as determined by SDS-PAGE (FIG. 4).

Example 3: Analysis of Activity of the Recombinant Polyphosphate-Dependent Glucokinase In this example, the activity of the recombinant polyphosphate-dependent glucokinase was analyzed. To this end, glucose (4% (w/v)), sodium hexametaphosphate (3% (w/v)), and $MgCl_2$ (1 mM) were suspended in 50 mM Tris-HCl buffer (pH 7.0) to prepare a reaction composition for analysis of activity. The purified enzyme (0.1 mg/ml) was added to the reaction composition. The reaction was allowed to proceed at 60° C. for 15 min. The reaction product was analyzed by HPLC under the following conditions: Aminex HPX-87C (Bio-rad) column, 80° C., 5 mM $H_2SO_4$ solution as mobile phase, and flow rate of 0.6 ml/min. Glucose 6-phosphate was detected and analyzed using a Refractive Index Detector.

The results of analysis revealed the production of glucose 6-phosphate from the reaction product of the purified recombinant enzyme.

Example 4: Analysis of pH-Dependent Activity of the Recombinant Polyphosphate-Dependent Glucokinase In this example, the influence of pH on the activity of the inventive enzyme was investigated. To this end, glucose (4% (w/v)), sodium hexametaphosphate (3% (w/v)), and $MgCl_2$ (1 mM) were suspended in 50 mM buffers of varying pH levels (sodium citrate, pH 4-7; sodium acetate, pH 4-7; Tris-HCl pH 7-10) to prepare reaction compositions for analysis of pH effect. The purified enzyme (0.1 mg/ml) was added to each of the reaction compositions. The reaction was allowed to proceed at 60° C. for 15 min. Thereafter, the production of glucose 6-phosphate was quantitatively analyzed by HPLC.

The results are shown in FIG. 5. The polyphosphate-dependent glucokinase derived from *Anaerolinea thermophila* of the present invention showed a maximum activity around pH 4-5, unlike enzymes reported to date. Particularly, the activity of the enzyme was found to be higher in the sodium acetate buffer than in the other buffers in the corresponding pH range. In addition, the activities of the enzyme in the wide pH range of 4-10 were >70% of the maximum activity (FIG. 5).

The novel characteristic of the polyphosphate-dependent glucokinase of the present invention is acidophilicity and high temperature activity, which enable efficient production of glucose 6-phosphate from starch dextrin when the inventive enzyme is used in combination with a glucoamylase derived from *Aspergillus* sp. (e.g., commercial glucoamylase AMG 300L (Novozymes) derived from *Aspergillus niger*). The commercial glucoamylase has an optimum activity at pH 4.5 and 60° C. The inventive enzyme is considered industrially very useful because its activities in the wide pH range of 4-10 are >70% of the maximum activity.

Example 5: Analysis of Temperature-Dependent Activity of the Recombinant Polyphosphate-Dependent Glucokinase In this example, the temperature-dependent activity of the recombinant enzyme was analyzed. To this end, glucose (4% (w/v)), sodium hexametaphosphate (3% (w/v)), and $MgCl_2$ (1 mM) were suspended in 50 mM Tris-HCl buffer (pH 7.0) to prepare a reaction composition for analysis of temperature-dependent activity of the recombinant enzyme. The purified enzyme (0.1 mg/ml) was added to the reaction composition. The reaction was allowed to proceed at 40° C. to 80° C. for 15 min. Thereafter, the production of glucose 6-phosphate was quantitatively analyzed by HPLC.

The results are shown in FIG. 6. The inventive enzyme showed a maximum activity at around 65-70° C. In addition, the activities of the enzyme in the wide temperature range of 60-80° C. were >95% of the maximum activity (FIG. 6).

Enzymes derived from *Thermobifida fusca* are known to be active at and thermoresistant to high temperature among polyphosphate-dependent glucokinases reported to date and were reported to be optimally active at a temperature of 55° C. [see Liao et al. 2012. Appl Microbiol Biotechnol 93:1109-1117].

Therefore, it can be concluded that the *Anaerolinea thermophila*-derived polyphosphate-dependent glucokinase of the present invention is more active at high temperature than any polyphosphate-dependent glucokinase reported to date, which is demonstrated by its optimum activity at 65-70° C.

Example 6: Analysis of Activity of the Recombinant Polyphosphate-Dependent Glucokinase Depending on the Kind of Metal Ions Polyphosphate-dependent glucokinases reported to date are known to demand metal ions such as $Mg^{2+}$, $Mn^{2+}$, $Co^{2+}$, and $Zn^{2+}$ for activity. In this example, the influence of metal ions on the activity of the inventive polyphosphate-dependent glucokinase was investigated. To this end, the inventive enzyme was treated with 10 mM EDTA, followed by dialysis to prepare an enzyme sample. Glucose (2% (w/v)), sodium hexametaphosphate (1.5% (w/v)), and metal ions ($NiSO_4$, $CuSO_4$, $MnSO_4$, $CaCl_2$, $ZnSO_4$, $MgSO_4$, $MgCl_2$, $FeSO_4$, NaCl, LiCl, and KCl, 1 mM each) were suspended in 50 mM Tris-HCl buffer (pH 7.0) to prepare reaction compositions. The metal ion-free enzyme sample (0.1 mg/ml) was added to each of the reaction compositions. The reaction was allowed to proceed at 60° C. for 15 min. Thereafter, the production of glucose 6-phosphate was quantitatively analyzed by HPLC. The activity of the enzyme sample untreated with metal ions was compared with the activities of the enzyme samples treated with metal ions.

As a result, the polyphosphate-dependent glucokinase derived from *Anaerolinea thermophila* showed demand for the metal ions such as Mg, Mn, Zn, Fe, and Ni for its activity, as shown in FIG. 7. The magnesium ions were more effective than the other metal ions, which was similarly observed in enzymes reported to date. Particularly, the addition of $MgSO_4$ was found to achieve a maximum activity (FIG. 7).

Example 6: Analysis of Temperature Stability of the Recombinant Polyphosphate-Dependent Glucokinase The temperature stability of the inventive polyphosphate-dependent glucokinase was analyzed. To this end, the purified recombinant enzyme (0.2 mg/ml) was heated to temperatures of 55-65° C. for different periods of time, and residual activities were compared and analyzed.

Glucose (4% (w/v)), sodium hexametaphosphate (3% (w/v)), and $MgCl_2$ (1 mM) were suspended in 50 mM Tris-HCl buffer (pH 7.0) to prepare a reaction composition. Each of the enzyme sample (0.1 mg/ml) heated to different temperatures was added to the reaction composition for analysis of residual activity. The reaction was allowed to proceed at 60° C. for 15 min. Thereafter, the production of glucose 6-phosphate was quantitatively analyzed by HPLC.

The results are shown in FIG. 8. A reduction in the activity of the enzyme was not observed at 55° C. for 6 h. The enzyme lost its activity of about 49% after 4 h at 60° C. The activity of the enzyme was maintained at about 62% of its initial value even at 65° C. for 0.5 h (FIG. 8).

*Thermobifida fusca*-derived enzymes are known to be more thermoresistant than any polyphosphate-dependent glucokinase reported to date and were reported to lose their activity (by 50%) after heating at 50° C. for 0.25 h. Although *Thermobifida fusca*-derived enzymes were immobilized for better heat resistance, their activity was reduced to 50% of their initial activity after 2 h [see Liao et al. 2012. Appl Microbiol Biotechnol 93:1109-1117].

Therefore, it can be concluded that the *Anaerolinea thermophila*-derived polyphosphate-dependent glucokinase of the present invention is most thermostable of enzymes reported to date because the activity of the inventive enzyme is maintained at about 51% of its initial value even after heating at 60° C. for 4 h.

Example 7: Analysis of Conversion Yields at Different Concentrations of the Substrates The conversion yields of glucose 6-phosphate at different concentrations of glucose and sodium hexametaphosphate were analyzed. To this end, glucose (2-15% (w/v)), sodium hexametaphosphate (1.5-11.5% (w/v)), and $MgSO_4$ (10 mM) were suspended in 50 mM Tris-HCl buffer (pH 7.0) to prepare reaction compositions. The purified enzyme (10-50 U/ml) was added to each of the reaction composition. The reaction was allowed to proceed at 55° C. for 12 h. Thereafter, the production of glucose 6-phosphate was quantitatively analyzed by HPLC.

As a result, the use of 2% (w/v) glucose and 1.5% (w/v) sodium hexametaphosphate achieved a conversion yield of 81% after reaction for 12 h. The use of 5% (w/v) glucose and 3.5% (w/v) sodium hexametaphosphate achieved a conversion yield of 78% after reaction for 12 h. The use of 10% (w/v) glucose and 7% (w/v) sodium hexametaphosphate achieved a conversion yield of 77% after reaction for 12 h. The use of 15% (w/v) glucose and 10% (w/v) sodium hexametaphosphate achieved a conversion yield of 65% after reaction for 12 h.

| Applicant's or agent's file reference: P16-6262 | International application No. |

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 16, line 116.

B. IDENTIFICATION OF DEPOSIT — Further deposits are identified on an additional sheet ☐

Name of depositary institution
Korean Culture Center of Microorganisms (KCCM)

Address of depositary institution (including postal code and country)
120-861, Yurim Building, Hongjenae-2ga-gil 45, Seodaemun-Gu, Seoul, Korea

| Date of deposit: February 16, 2016 | Accession Number: KCCM11814P |

C. ADDITIONAL INDICATIONS (leave blank if not applicable) — This information is continued on an additional sheet ☐

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
| ☐ This sheet was received with the international application | ☐ This sheet was received by the International Bureau on: |
| Authorized officer | Authorized officer |

Form PCT/RO/134 (July 1998; reprint January 2004)

The invention claimed is:

1. A method for producing glucose 6-phosphate, comprising (a) contacting a composition comprising a thermoresistant polyphosphate-dependent glucokinase having the amino acid sequence of SEQ ID NO. 2 or having the amino acid sequence which has at least 95% sequence identity to SEQ ID NO. 2 with glucose and polyphosphate at a temperature of 60-80° C.,
   wherein the glucokinase has a maximum activity at 65-70° C. and has activities of 95% or more relative to the maximum activity in the whole range of 60–80° C.

2. The method according to claim 1, wherein the glucose is prepared by (b) contacting liquefying and saccharifying enzyme with starch or cellulose.

3. The method according to claim 1, wherein the polyphosphate is sodium hexametaphosphate.

4. The method according to claim 1, wherein the glucose 6-phosphate is produced at a pH of 4 to 10.

5. The method according to claim 1, wherein the composition further comprises magnesium ions.

6. The method according to claim 1, wherein the polyphosphate-dependent glucokinase is present in an amount of 10 U/ml to 50 U/ml.

7. The method according to claim 1, wherein the glucose is present in an amount of 0.1% to 40% by weight, based on the total weight of the composition.

8. The method according to claim 1, wherein the polyphosphate is present in an amount of 0.5% to 25% by weight, based on the total weight of the composition.

9. The method according to claim 2, wherein the liquefying and saccharifying enzymes is one or more selected from alpha-amylases, glucoamylases and alpha-glycosidases.

10. The method according to claim 2, wherein the step (a) and the step (b) is one-pot enzymatic conversion.

* * * * *